(12) United States Patent
Tuma et al.

(10) Patent No.: US 8,231,554 B2
(45) Date of Patent: Jul. 31, 2012

(54) METHOD AND DEVICE FOR REGISTERING A FEMUR IMPLANT

(75) Inventors: Gregor Tuma, München (DE); Mario Schubert, Landsham (DE); Peter Drumm, München (DE); Claus Schaffrath, München (DE)

(73) Assignee: BrainLAB AG, Kircheim/Heimstetten (DE)

( * ) Notice: Subject to any disclaimer, the term of this patent is extended or adjusted under 35 U.S.C. 154(b) by 2802 days.

(21) Appl. No.: 10/701,367

(22) Filed: Nov. 4, 2003

(65) Prior Publication Data

US 2004/0143340 A1 Jul. 22, 2004

Related U.S. Application Data

(60) Provisional application No. 60/440,701, filed on Jan. 17, 2003.

(30) Foreign Application Priority Data

Nov. 5, 2002 (EP) ..................................... 02024596

(51) Int. Cl.
*A61B 5/103* (2006.01)
*A61B 5/117* (2006.01)

(52) U.S. Cl. ....................................... 600/595; 600/587

(58) Field of Classification Search ................... 600/595, 600/587; 700/302; 623/22.12, 914; 606/102
See application file for complete search history.

(56) References Cited

U.S. PATENT DOCUMENTS

| 5,888,245 | A |   | 3/1999  | Meulink et al. |
|-----------|---|---|---------|----------------|
| 6,002,859 | A | * | 12/1999 | DiGioia et al. ................. 703/11 |
| 6,370,418 | B1|   | 4/2002  | Bernoski       |

FOREIGN PATENT DOCUMENTS

| WO | 01/64143  | 9/2001  |
|----|-----------|---------|
| WO | 02/071987 | 9/2002  |
| WO | 02/080824 | 10/2002 |

* cited by examiner

*Primary Examiner* — Jeffrey G Hoekstra
(74) *Attorney, Agent, or Firm* — Renner, Otto, Boisselle & Sklar, LLP

(57) ABSTRACT

A method for registering an asymmetrical femur implant having a shaft and a collar includes ascertaining a position of a shaft axis associated with the shaft and ascertaining a position of a collar axis associated with the collar. A device for registering an asymmetrical femur implant connected to at least one reference marker is provided. The device includes a detection device for detecting a spatial position of the at least one reference marker and a database in which a geometry of the asymmetrical femur implant is stored. A processor ascertains the spatial position of the asymmetrical femur implant.

10 Claims, 2 Drawing Sheets

METHOD AND DEVICE FOR REGISTERING A FEMUR IMPLANT

RELATED APPLICATION DATA

This application claims priority of U.S. Provisional Application No. 60/440,701, filed on Jan. 17, 2003, which is incorporated herein by reference in its entirety.

FIELD OF THE INVENTION

The invention relates generally to the field of preparing, performing and verifying the implantation of artificial joint components and, more particularly to preparing the computer-assisted implantation of a femur implant during a hip operation. The present invention relates to a method and device for registering and/or navigating and/or positioning a femur implant.

BACKGROUND OF THE INVENTION

Artificial hip joints are known in which a femur implant is inserted into a bodily upper leg bone (femur), once a bodily joint head has been removed, and anchored or fastened in the bone. A spherical or partially spherical head, which may be attached to the femur implant or is fixedly connected to the femur implant can be accommodated by an abutment, such as, for example, a joint cavity, in the manner of a ball joint.

A typical femur implant can include a shaft made of, for example, titanium or plastic, and tapering conically downwards. The implant can be inserted into an upper leg bone once the bodily joint head has been removed. The shaft passes into a collar and a joint or femur head can be provided on the front side of the collar. The spatial position of the femur implant can be defined, for example, by determining the positions of the collar axis and the shaft axis. In general, femur implants designed in other ways, e.g. modularly, can also be used.

Seating the femur implant precisely in the upper leg bone is a decisive criterion for the success of implanting a hip joint. Even the smallest deviations can lead to increased wear and, therefore, to a reduced service life of the hip joint implant. If the femur implant is not positioned precisely in the upper leg bone, then the femur head of the femur implant arranged in the acetabular component or cavity can easily be dislocated, in particular, if sudden stresses or impacts act on the artificially inserted hip joint. If the hip joint components are not precisely positioned, suddenly occurring stresses can easily lead to the femur head or the collar axis of the femur implant colliding with either the rim of a corresponding cavity or soft tissue or a bone structure surrounding the implant. Correspondingly, precisely positioning the individual components of an artificial hip joint and in particular precisely positioning the femur implant is essential for a successful operation and a long service life of the joint as a whole.

A device and a method for implanting artificial joint components are known from U.S. Pat. No. 6,002,859. This proposes determining the position of the implant by simulation and tracking the hip, the hip joint cavity and the femur implant using an optical system. In this way, so-called targets are attached to bones and tools for inserting the artificial joint components. In one embodiment, the insertion of artificial, axially symmetrical hip joint components is described. However, the conventional process may be deficient when dealing with asymmetrical implants and other complicating factors.

SUMMARY OF THE INVENTION

It is an object of the present invention to propose a method and a device for registering an asymmetrical femur implant, which enable an axially-asymmetrical femur implant to be precisely positioned at a desired point in an upper leg bone.

In accordance with one embodiment, a method includes registering an asymmetrical femur implant by attaching a marker, such as, for example, a reference star, directly to the asymmetrical femur implant. For example, the reference star can be attached to the extended collar axis or shaft axis, in order to ascertain the spatial position or orientation of a first femur implant axis, such as, for example, the collar axis or the shaft axis. Since the spatial position of an asymmetrical implant is not yet defined by determining the position of one axis, the femur implant can be registered in accordance with a first aspect of the invention by a tip of a pointer instrument including one or more attached markers pointing to a reference region or reference point of the femur implant. For example, the reference region or point can include an indentation or characteristic form provided in the femur implant, such that the asymmetrical femur implant can be completely referenced by determining the second axis in this way, in order to precisely define the spatial position of the femur implant. The exact spatial position of the femur implant, including the course of the collar axis and shaft axis, can be ascertained by the referencing performed in accordance with the invention.

In accordance with another aspect of the invention, the asymmetrical femur implant can be referenced by ascertaining the position of at least one marker or reference star attached directly to the femur implant, in order, for example, to ascertain the spatial orientation of the collar axis or the shaft axis of the femur implant. Furthermore, a region of the femur implant, such as, for example, a pointed end region of the shaft of the femur implant can be placed or inserted onto a predetermined point of a referencing or calibrating element, to which, in turn, at least one marker or reference star is also attached, in order to ascertain the position of the second axis. A planar plate including an indentation provided therein at a particular point can be used as the referencing element. The pointed end region of the shaft can then be inserted into the indentation on the referencing element and the femur implant can optionally be moved relative to the referencing element. In this way, the complete spatial position of the femur implant can be ascertained from the known spatial position of the referencing element and the spatial position of the femur implant partially established by at least one marker, provided that the assumption that the implant has been inserted into the indentation. The movement or tipping and/or pivoting of the femur implant relative to the referencing element can be used to even more precisely determine the spatial position and thus completely register the femur implant.

The second implant axis can equally be ascertained without a calibrating element by fixing the position of the tip of the implant. For example, the tip of the implant can be inserted into any given positionally stable indentation. A movement of the implant fixed on the tip in this way can lead to the reference geometry connected to the implant and including one or more markers describing a spherical segment. The center point of the sphere, which corresponds to the tip of the implant, can be calculated from this spherical segment. In this way, the implant can be completely referenced.

In accordance with another aspect of the present invention, at least two markers or reference stars can be attached to the asymmetrical femur implant in order to ascertain the spatial position of the collar axis and the shaft axis of the femur implant, and therefore, to register the femur implant.

In one embodiment, the at least one marker or reference star attached to the femur implant can be attached approximately or precisely to an extension of one of the axes describing the spatial position of the femur implant. It can be advantageous if a reference star is attached to the femur implant in such a way that a reference point of the reference star, known due to the marker geometry, lies on the center axis of one of the axes determining the position of the femur implant. For example, a marker or reference star can be attached, in the direction of an extension of the collar axis of the femur implant, to or instead of the femur head. Further, the marker or reference star can be attached to the femur implant along an extension of the shaft axis, such as, for example, the pointed end of the femur implant or the end of the femur implant opposite the pointed end.

Once registration is complete, the spatial position of a femur implant registered in accordance with the invention is known. This can then be navigated to a desired point. Furthermore, if the spatial position of the upper leg bone is, for example, known via a reference star connected to the upper leg bone, then the femur implant registered in accordance with the invention can be precisely positioned in the upper leg bone.

In one embodiment, a desired or correct position of the femur implant can be calculated in advance by simulation, such as is described in U.S. Pat. No. 6,002,859, which is incorporated herein by reference in its entirety. Based on imaging methods, such as, for example, computer tomography, the most advantageous position of the hip joint endoprosthesis and, therefore, of the femur implant can be ascertained individually for a patient.

In general, a distinction can be made between implants fastened in a bone with cement or without cement. Implants attached without cement can be inserted into a cut-open channel in the marrow of the upper leg bone and substantially held in the upper leg bone by pressure fitting. The method in accordance with the invention can advantageously be used with femur implants cemented in an upper leg bone and/or fastened in an upper leg bone with cement. In embodiments including implant methods using cement, a greater volume than that of the femur implant to be inserted is removed from the upper leg bone in a preparatory incision. Cement and the femur implant are then inserted into the upper leg bone, such that the femur implant still moves relative to the upper leg bone and can thus be positioned as exactly as possible before the cement hardens. In the case of cemented implants, femur implants registered and navigated in accordance with the invention can still be easily orientated and positioned. Registering and navigating the femur implant in accordance with the invention leads to increased precision in comparison to known methods.

Since the femur implant can be registered and navigated by at least one marker or reference star attached directly to the femur implant, the precision when ascertaining the position of the femur implant is greater in comparison to methods, such as, for example, that known from U.S. Pat. No. 6,002,859, in which tools and devices for preparing and inserting the femur implant are navigated because the position of the femur implant to be navigated is only indirectly detected. Therefore, the precision in ascertaining the position of a femur implant can be improved using the method in accordance with the invention by directly determining the position of the implant.

The method in accordance with the invention can also advantageously be used to verify the position of a femur implant inserted into an upper leg bone, in order, for example, to ascertain parameters which are essential for correctly positioning and correctly seating an implant and, therefore, for a long service life of the implant. Examples of such parameters include the position of the rotational center point of the hip joint, the length of the leg, the anteversion of the femur head, the depth of insertion of the femur implant; anterior/posterior shift, (i.e., parallel shifting of the implant with respect to the upper leg bone shaft axis in the anterior-posterior direction (abdomen-back)), anterior/posterior tilt, (i.e., rotation of the implant about the intersecting point of the shaft axis and collar axis in the anterior-posterior direction), lateral-medial shift, (i.e., parallel shifting of the implant with respect to the upper leg bone shaft axis in the lateral-medial direction (left-right and/or outside-center)), and varus/valgus tilt, (i.e., rotation of the implant about the intersecting point of the shaft axis and collar axis in the lateral-medial direction).

In accordance with another aspect, the invention relates to a computer program which, when it is loaded onto a computer or is running on a computer, performs one or more of the method steps described above. Furthermore, the invention relates to a storage medium for such a program or to a computer program product comprising such a program.

According to another aspect of the invention, a device for registering and/or navigating and/or positioning an asymmetrical femur implant includes a detection device, such as, for example, optical cameras for detecting infrared radiation, or a system based on sound waves or radio waves or another suitable device for detecting positional signals emitted or reflected for example by markers. Furthermore, a database can provided in which data on the geometry and/or dimensions of one or more different femur implants is stored. In one embodiment, a computational unit is provided, which determines the spatial position of a femur implant from the positional signals provided by the detection device, wherein one or more of the methods described above for registering, navigating and/or positioning a femur implant may be used.

In accordance with another aspect, the invention relates to an asymmetrically formed femur implant including at least one fastening point for at least one marker or reference star. The at least one marker, or a point of origin of the reference star which may be freely determined and is to ascertained for example by software, can be arranged on a collar axis or a shaft axis of the femur implant.

The end region of the femur implant, to which a, for example, spherical or partially spherical femur head can be attached, is advantageously formed such that at least one marker or reference star can be fastened to the end portion of the collar axis or, alternatively, also to the femur head. The connection between the femur implant and the attached marker or reference star can be formed such that the at least one marker or reference star is arranged or fastened non-rotationally on the femur implant and can easily be removed again.

The marker or markers and the reference star or reference stars attached to the femur implant can be mounted non-rotationally with respect to the femur implant. This can be realized, for example, by appropriate geometries, such as grooves with which rotational blocks mesh, by positive-lock connections or by non-positive-lock connections such as, for example, anti-slip or rubber-like elements abutting corresponding counter surfaces. It can be advantageous to attach one or more markers or reference stars to the femur implant in such a way that they cannot easily be moved, (i.e., only by greater forces than those which occur under normal stress).

In accordance with one embodiment, a reference region is provided on the implant, such as, for example, an indentation or a characteristic surface form and/or surface structure, which can be pointed to by a pointer instrument or which a pointer instrument can be inserted or placed into, in order to be able to register the femur implant.

In accordance with another aspect, the present invention relates to a system including a femur implant as described above and a referencing element, such as, for example, a point instrument, which can be placed onto one or more predetermined or freely selectable points on the femur implant. The system can include a referencing device, such as, for example, a plate-like device provided with at least one marker or reference star and having a predetermined contact point, such as an indentation into which a particular region of the femur implant, such as, for example, an outer end of the shaft axis, can be inserted and moved or pivoted relative to the referencing device.

BRIEF DESCRIPTION OF THE DRAWINGS

These and further features of the present invention will be apparent with reference to the following description and drawings, wherein.

DETAILED DESCRIPTION OF THE INVENTION

Figure 1:
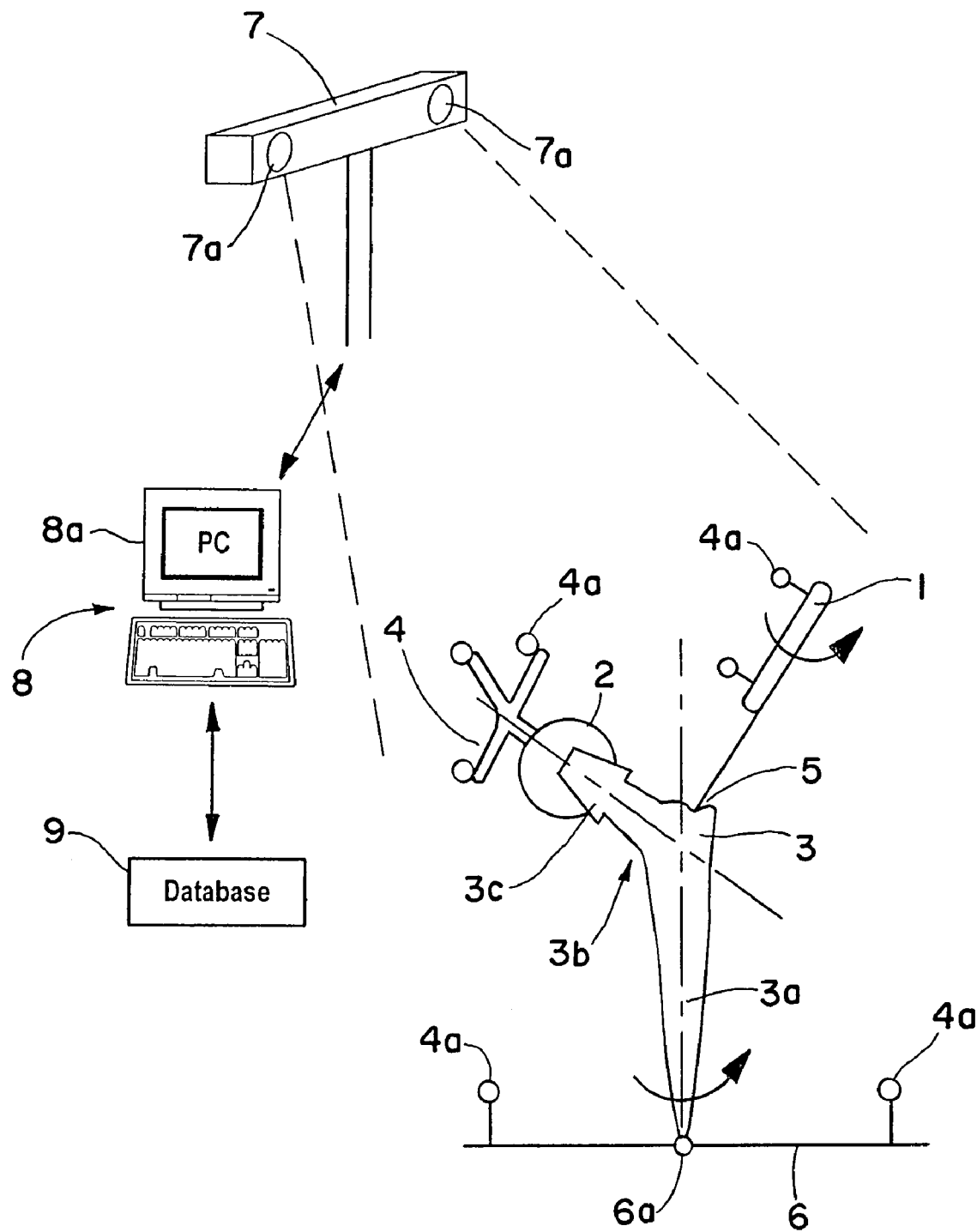
FIG. 1 is a diagrammatic illustration of a registering system and femur implant including registering elements in accordance with the present invention.

FIG. 1 illustrates a femur implant 3 including a shaft 3a and a collar 3b arranged at an angle to the shaft 3a. The position of the shaft 3a can be defined by the shaft axis indicated by a dot-dash line and the position of the collar 3b can be defined by the collar axis indicated by a dot-dash line. A front end of the collar 3b can include a truncated element 3c. In one embodiment, an approximately spherical femur head 2 can be fastened to the truncated element 3c. Alternatively, an adaptor element for attaching a reference star 4 can be attached to the truncated element 3c. The reference star 4 can include one or more markers 4a arranged and fastened thereon, preferably non-rotationally, for registering, navigating and/or positioning the implant 3. Navigation is described in greater detail in commonly assigned U.S. Pat. No. 6,351,659, which is incorporated herein by reference in its entirety.

The femur implant 3 can be registered by ascertaining the collar axis using the position of the reference star 4 placed on the collar 3b. In one embodiment, the position of the shaft 3a can be determined using a pointer instrument 1 to which markers 4a are attached. The pointer instrument 1 can be positioned at a predetermined reference region or indentation 5 of the femur implant 3 and moved, for example, as shown by the arrow, in order to ascertain the spatial position of the reference region 5 and thus the position of the shaft axis.

In accordance with another embodiment, the femur implant 3 can be registered by placing or inserting a particular region of the femur implant 3, such as, for example, the pointed end of the shaft 3a, on or into a reference region 6a or a reference point of a referencing element 6. The pointed end of the shaft 3a can be tipped or pivoted therein as shown by the other arrow in FIG. 1, in order to ascertain the orientation of the shaft axis.

Alternatively or in addition, further markers or reference stars can also be attached to the femur implant 3, wherein care must be taken that the femur implants cannot be altered in any way, since they are subject to specific approval procedures.

FIG. 1 also shows a detection device 7 including two IR cameras 7a in order to detect the signals emitted and/or reflected by the markers 4a. The positional signals of the markers 4a detected by the detection device 7 can be transmitted to a computational unit or processor 8, including a corresponding data base 9, in order to ascertain the position of the femur implant 3. The femur implant 3 can be registered and can be navigated or positioned at a particular point. Positional information on the implant 3 can for example be displayed on a screen 8a.

Figure 2:
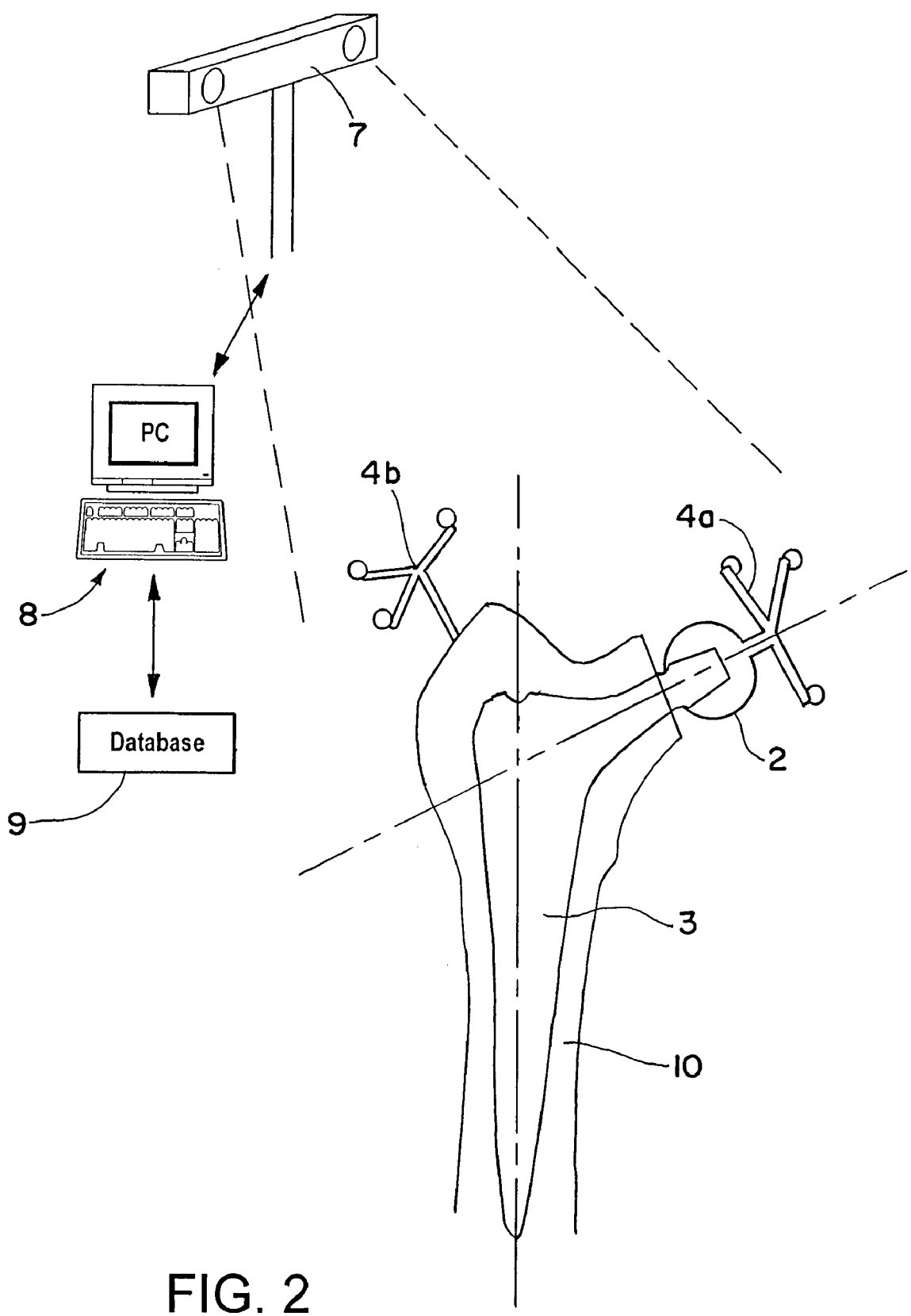
FIG. 2 is a diagrammatic illustration of a registering system and a femur implant inserted into a bone in accordance with the present invention.

FIG. 2 shows the implant 3 inserted into an upper leg bone 10. The implant 3 can be precisely positioned in the bone 10, whose position is ascertained using the reference star 4b, by using positional data on the implant 3 obtained via the reference star 4a, which is connected to the implant 3.

Although particular embodiments of the invention have been described in detail, it is understood that the invention is not limited correspondingly in scope, but includes all changes, modifications and equivalents.

The invention claimed is:

1. A method for registering in a surgical navigation system an asymmetrical femur implant having a shaft and a collar, said method comprising:
    determining a position of a shaft axis associated with the shaft;
    determining a position of a collar axis associated with the collar;
    registering in the surgical navigation system a position of the asymmetrical femur implant based on the determined position of the shaft axis and the determined position of the collar axis.

2. The method as set forth in claim 1, wherein determining the position of the shaft axis and/or determining the position of the collar axis includes detecting a position of at least one reference marker attached to the asymmetrical femur implant.

3. The method as set forth in claim 1, wherein determining the position of the shaft axis and/or determining the position of the collar axis includes detecting a position of at least one reference star attached to the asymmetrical femur implant.

4. The method as set forth in claim 1, wherein determining the position of the shaft axis and/or determining the position of the collar axis is performed using a pointer instrument.

5. The method as set forth in claim 4, wherein at least one marker is attached to the pointer instrument.

6. The method as set forth in claim 4, wherein at least one reference star is attached to the pointer instrument.

7. The method as set forth in claim 1, wherein determining the position of the shaft axis and/or determining the position of the collar axis is performed using a referencing element onto which the asymmetrical femur implant is set.

8. The method as set forth in claim 7, wherein at least one marker is attached to the referencing element.

9. The method as set forth in claim 7, wherein at least one reference star is attached to the referencing element.

10. A non-transitory computer-readable storage medium including a computer program, wherein when the program is loaded onto a computer and executed, the program causes the computer to carry out the steps as set forth in claim 1.

* * * * *